(12) United States Patent
Glasenapp

(10) Patent No.: US 11,099,100 B2
(45) Date of Patent: Aug. 24, 2021

(54) METHOD AND DEVICE FOR MEASURING AN OPTICAL LENS FOR INDIVIDUAL WEARING SITUATIONS BY A USER

(71) Applicant: Carl Zeiss Vision International GmbH, Aalen (DE)

(72) Inventor: Carsten Glasenapp, Oberkochen (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 17/074,710

(22) Filed: Oct. 20, 2020

(65) Prior Publication Data
US 2021/0033489 A1    Feb. 4, 2021

Related U.S. Application Data

(63) Continuation of application No. PCT/EP2019/060346, filed on Apr. 23, 2019.

(30) Foreign Application Priority Data

Apr. 23, 2018 (EP) .................................... 18168823

(51) Int. Cl.
*G01M 11/02* (2006.01)
*G02C 7/02* (2006.01)

(52) U.S. Cl.
CPC ......... *G01M 11/0264* (2013.01); *G02C 7/024* (2013.01); *G01M 11/0214* (2013.01)

(58) Field of Classification Search
CPC ......... G01M 11/0264; G01M 11/0214; G01M 11/0221–025; G01B 11/245; G02C 7/024
See application file for complete search history.

(56) References Cited

U.S. PATENT DOCUMENTS 8,042,280 B2   10/2011   Watanabe et al.
9,797,804 B2   10/2017   Glasenapp et al.
(Continued)

FOREIGN PATENT DOCUMENTS

CN     101952682 A     1/2011
CN     105528777 A     4/2016
(Continued)

OTHER PUBLICATIONS

International Preliminary Examination Report issued in PCT/EP2019/060346, to which this application claims priority, dated Apr. 15, 2020, and English-language translation thereof.
(Continued)

*Primary Examiner* — Hina F Ayub
*Assistant Examiner* — Amanda Merlino
(74) *Attorney, Agent, or Firm* — Thrive IP®; Georg M. Hasselmann

(57) ABSTRACT

A device for measuring the optical effect of an ophthalmic lens, in particular a spectacle lens, includes a display system, an image acquisition system, and a computer unit. During measurement, the lens is arranged in a measurement volume of the device. The display system displays a test structure and the image acquisition system acquires image data of the test structure from multiple viewpoints using imaging optical paths which pass through the lens. The computer unit determines the three-dimensional shape of the lens on the basis of the image data and calculates an optical effect of the lens on the basis of its three-dimensional shape. A corresponding method and computer program are also disclosed.

18 Claims, 10 Drawing Sheets

(56) References Cited

U.S. PATENT DOCUMENTS

| | | |
|---|---|---|
| 10,430,962 B2 | 10/2019 | Seto |
| 10,520,390 B2 | 12/2019 | Glasenapp et al. |
| 2014/0300856 A1 | 10/2014 | Dangelmaier et al. |
| 2016/0109362 A1 | 4/2016 | Kubiak et al. |
| 2016/0143524 A1 | 5/2016 | Bérard et al. |

FOREIGN PATENT DOCUMENTS

| | | |
|---|---|---|
| CN | 107810400 A | 3/2018 |
| CN | 107869966 A | 4/2018 |
| DE | 1238690 B1 | 4/1967 |
| DE | 102011089704 A1 | 6/2013 |
| DE | 102013219838 A1 | 4/2015 |
| DE | 102014005281 A1 | 10/2015 |
| EP | 2101143 A1 | 9/2009 |
| JP | 2017181298 A | 10/2017 |
| KR | 1020180019123 A | 2/2018 |
| WO | 2016207412 A1 | 12/2016 |
| WO | 2017134275 A1 | 8/2017 |
| WO | 2018052455 A1 | 9/2018 |

OTHER PUBLICATIONS

"Ophthalmic optics—Spectacle lenses—Vocabulary (ISO 13666:2012);" German and English version EN ISO 13666:2012, Oct. 2013.

Knauer et al., "Measuring the refractive power with deflectometry in transmission," DGaO Proceedings, 2008.

Extended European Search Report issued in EP 18168823.5, to which this application claims priority, dated Sep. 11, 2018, and English-language translation thereof.

International Search Report issued in PCT/EP2019/060346, to which this application claims priority, dated Oct. 23, 2019, and English-language translation thereof.

Office action by the Korean Patent Office issued in KR10-2020-7030591, which is a counterpart hereof, dated Jan. 11, 2021, and English-language translation thereof.

Extended European Search report issued in EP 21168318.0, which is a counterpart hereof, dated Jun. 24, 2021, and English-language machine translation thereof.

Office action by the Chinese patent office (CIPO) issued in CN201980027633.2, which is a counterpart hereof, dated May 6, 2021, and English-language machine translation thereof.

METHOD AND DEVICE FOR MEASURING AN OPTICAL LENS FOR INDIVIDUAL WEARING SITUATIONS BY A USER

CROSS REFERENCE TO RELATED APPLICATIONS

This application is a continuation application of international patent application PCT/EP2019/060346, filed Apr. 23, 2019, designating the United States and claiming priority from European patent application EP 18168823.5, filed Apr. 23, 2018, and the entire content of both applications is incorporated herein by reference.

TECHNICAL FIELD

The present disclosure relates to the field of ophthalmic optics and, in particular, an apparatus for measuring the optical effect of an optical lens, in particular a spectacle lens, arranged in a measurement volume. The present disclosure further relates to an apparatus for measuring a spatial refractive index distribution of an optical lens, in particular a spectacle lens, arranged in a measurement volume. The present disclosure further relates to a method for calibrating a corresponding apparatus and a computer-implemented method for measuring the optical effect of an optical lens arranged in a measurement volume.

BACKGROUND

The measurement value usually of interest in the case of spectacle lenses is the vertex power (VP). The vertex power is an effective variable of the lens under certain observation situations. Consequently, the VP differs, depending on the distance to the observer or the lens tilt. A measurement appliance which ascertains a VP by way of a direct interpretation of the light beams passing through a lens will always determine a VP in this measurement appliance configuration. Such effective variables only have a limited use for an unambiguous qualification of a component. Therefore, the ISO VP was defined to remedy this. The ISO VP is the VP measured perpendicular to the surface normal in the case of a parallel incidence of light. To this end, specific measurement appliances have been developed in the past, which determine the ISO VP at individual positions of a lens.

The advantage of the ISO VP is that it is a unique component variable and not an effective variable like the VP. A disadvantage is that the ISO VP can deviate from the effect of a pair of spectacles in the worn situation (also referred to as the worn vertex power or worn value).

A lensmeter with a spectacles installation for checking ready glazed spectacles is known from DE 1 238 690 B1. Using this, it is possible to determine the vertex power of a spectacle lens already set in a frame.

EP 2 101 143 A1 discloses a method and an apparatus for capturing the shape of transparent refractive objects. In the method for capturing the shape of transparent refractive objects, the object to be measured is inserted in transmission into an imaging system. Using the modified imaging system created in this way, a grid with a known structure is imaged onto a receiver device and the arising image is evaluated. Use is made of planar grids with known structures, the grid points of which are assigned to evaluable spatial coordinates in grid coordinate systems. One or more of these planar grids is inserted at least at two different positions with respect to the object to be measured.

US 2016/0109362 A1 discloses a method and apparatus for determining a local refractive index.

Knauer et al., "Measuring the refractive power with deflectometry in transmission," DGaO Proceedings, 2008, describes a deflectometric method for determining the refractive power.

WO 2017/134275 A1 describes methods and systems for determining an optical axis and/or physical properties of a lens and the use of same in virtual imaging and in the case of head-mounted display devices.

WO 2016/207412 A1 discloses an apparatus and a method for measuring individual data of spectacles arranged in a measurement position, the spectacles having a left and/or a right spectacle lens. The apparatus comprises a display for displaying a test structure. The apparatus comprises an image capturing device for capturing the test structure with an imaging beam path that passes through the left spectacle lens and/or the right spectacle lens of the spectacles. The apparatus comprises a computer unit with a computer program which determines a refractive power distribution for at least a section of the left spectacle lens and/or the right spectacle lens from the image of the test structure captured by the image capturing device and a known spatial orientation of the display relative to the image capturing device and also a known spatial orientation of the spectacles relative to the image capturing device.

DE 10 2013 219 838 A1 discloses a method and system for ascertaining the spatial structure of an object. DE 10 2014 005 281 A1 discloses a method and an apparatus for determining the position of at least one spectacle lens in space. DE 10 2011 089 704 A1 discloses storage of information on a spectacle lens, spectacle lens blank or spectacle lens semifinished product.

The appliances known from the related art are effect measuring appliances, in which the effect of an optical element is initially determined in one measurement position.

SUMMARY

Against this background, it is an object of the present disclosure to provide a measurement apparatus which facilitates a more flexible determination of the optical effect of an optical lens.

According to a first aspect of the present disclosure, it is therefore proposed to provide an apparatus for measuring the optical effect of an optical lens, in particular the spectacle lens arranged in a measurement volume, comprising a display device which is configured to display a test structure; an image capturing device which is configured to capture image data of the test structure from a plurality of viewpoints by way of imaging beam paths which pass through the lens; and a computing unit, wherein the computing unit is configured to determine a three-dimensional shape of the lens on the basis of the image data; and calculate an optical effect of the lens on the basis of the three-dimensional shape thereof, wherein the lens is a spectacle lens. The computing unit is configured to calculate the optical effect of the spectacle lens for a specified wearing position of a user, which differs from the measurement position in which the image data are captured.

Compared to conventional lensmeters, substantial advantages of the disclosure may consist in an improved unambiguousness and/or range of application, in particular. A reason for this is that the optical effect of a lens always depends on the direction of passing radiation. A measuring appliance which only measures the optical effect can only determine the latter reliably for the case of the measurement arrangement. Very precise statements can already be made herewith for a multiplicity of applications.

However, a measurement situation and an actual wearing situation or wearing position of a spectacle lens might not coincide or might deviate from one another to such an extent that a reliable statement is no longer possible. Thus, a further measurement of the effect under wearing conditions would be required to determine the optical effect in the wearing position.

The solution according to the disclosure follows a different approach: A two-stage procedure is proposed, in which the three-dimensional shape of the lens is initially determined and only then is the optical effect of the lens calculated. A known three-dimensional shape or topography of the lens allows the optical effect to be calculated subsequently for any viewing or wearing situation. Advantages can comprise, in particular, more accurate results and more individualized statements for a wide range of user-specific requests.

The display unit displays a test structure. The test structure is captured by the image capturing device from a plurality of viewpoints. Since the test structure is known, an association can be made between image data of the test structure captured by the image capturing device for each of the plurality of viewpoints. If an optical lens is now placed into a measurement volume between the display device and the image capturing device, the beam paths between the respective pixels of the image data and the corresponding image elements of the test structure are influenced.

However, in the process, it is not possible to determine only a single virtual refractive plane, as indicated in WO 2016/207412 A1. By virtue of image data being captured from a plurality of viewpoints in accordance with the proposed solution, with the imaging beam paths passing through the lens, it is possible, in particular, to make separate statements about a shape of a front surface, through which beam paths emanating from the test structure enter into the optical lens, and statements about a shape of a back surface, via which beam paths emanating from the test structure emerge from the optical lens. Thus, a system of equations with a multiplicity of equations can be set up to this end, on the basis of which there can then be a reconstruction of the surfaces lying in the beam path. The three-dimensional shape of the lens follows, in turn, from the shape of the front surface and the shape of the back surface.

The calculation of the optical effect on the basis of the three-dimensional shape can be implemented thereafter using known methods.

It is understood that it is not necessary for the three-dimensional shape of the entire lens to be determined. By way of example, the calculation can be implemented only for a portion, for example only the front and back surface, without side faces, or only for a portion in a user's field of vision.

When determining the three-dimensional shape of the lens by the computing unit, more in-depth information, such as for example a known relative spatial position of the display device in relation to the respective viewpoints, from which the capture is implemented, can advantageously be taken into account.

According to a further aspect, an apparatus is proposed for measuring the optical effect of an optical lens arranged in a measurement volume, comprising a display device which is configured to display a test structure; an image capturing device which is configured to capture image data of the test structure from a plurality of viewpoints by way of imaging beam paths which pass through the lens; and a computing unit, wherein the computing unit is configured to: determine a three-dimensional shape of the lens on the basis of the image data; and calculate an optical effect of the lens on the basis of the three-dimensional shape thereof. The computing unit can be configured to determine the three-dimensional shape of the lens further taking account of one or more known contact points of the lens; wherein a position of the contact points is used to assign to an algorithm, which determines the shape of the spectacle lens, an expected value for the position of the latter in the measurement volume.

According to a further aspect of the present disclosure, an apparatus is proposed for measuring the optical effect of an optical lens arranged in a measurement volume, comprising a display device which is configured to display a test structure; an image capturing device which is configured to capture image data of the test structure from a plurality of viewpoints by way of imaging beam paths which pass through the lens; and a computing unit, wherein the computing unit is configured to: determine a three-dimensional shape of the lens on the basis of the image data; and calculate an optical effect of the lens on the basis of the three-dimensional shape thereof. The computing unit can be configured to determine the three-dimensional shape of the lens taking account of a boundary condition, wherein the boundary condition is determined by reading information about the lens to be measured, wherein the boundary condition is determined by reading a code on the lens.

According to a further exemplary aspect of the present disclosure, which may assist with the understanding of the disclosure, a method is provided for calibrating an apparatus for measuring individual data of an optical lens arranged in a measurement volume, wherein the method includes the following steps: providing or displaying a test structure on the display device; setting a first distance between the image capturing device and the display device and capturing image data of the test structure with the image capturing device from the first distance; setting a second distance between the image capturing device and the display device and capturing image data of the test structure with the image capturing device from the second distance; determining a direction of incident light beams, which are captured by the image capturing device, and corresponding pixels in the image data on the basis of the image data captured at the first distance and the image data captured at the second distance.

An advantage of this solution consists of the fact that the direction of incident light beams can be determined in a simple manner. Here, the display device used for the measurement in any case can also serve calibration purposes. The relative position of the display device including its image points relative to the image capturing device can typically be taken into account during the calibration.

As a result of the height adjustment, there is a change in the angle of the incident light beams relative to the image capturing device, for example relative to the cameras of the image capturing device. A direction of the incident light can be determined from a relationship between the known change in height and a change in an image representation of the test structure in the image data accompanying this. This facilitates so-called "back propagation" of the incident light beams.

According to a further aspect of the present disclosure, a method, in particular computer-implemented method, is disclosed for measuring the optical effect of an optical lens, in particular a spectacle lens, arranged in a measurement volume, including the steps of: providing a test structure for display on a display device; capturing image data of the test structure from a plurality of viewpoints by way of imaging beam paths which pass through the lens; determining a three-dimensional shape of the lens on the basis of image data; and calculating an optical effect of the lens on the basis of the three-dimensional shape thereof.

According to further aspects of the present disclosure, methods corresponding to the aforementioned aspects are proposed.

According to a further aspect of the present disclosure, a computer program product is proposed, comprising instructions that, upon execution of the program by a computer, cause the latter to carry out one of the aforementioned methods. It is understood that the method steps in this case are designed to be carried out by computer. By way of example, capturing image data can be understood to mean receiving image data. Thus, the term can be understood as a transmission of measurement data generated by a physical image sensor. Accordingly, the test structure can be provided by the provision of test structure data. In turn, the data can be displayed by a display device.

The provision of the test structure can also be a preceding step, which is not carried out by the computer program product.

If nothing else is specified, the terms used herein should be understood within the meaning of the standard DIN EN ISO 13666:2012 by the Deutsches Institut für Normung e.V. [German Institute for Standardization].

Pursuant to section 5.8 of the DIN EN ISO 13666:2012 standard, the term front surface or object-side surface denotes that surface of a spectacle lens intended to face away from the eye in the spectacles. Pursuant to section 5.19 of the DIN EN ISO 13666:2012 standard, the term back surface or eye-side surface denotes that surface of a spectacle lens intended to be fitted facing to the eye. As an alternative to this, the term front surface within the scope of the present disclosure can denote the surface of the lens facing the display device. Accordingly, a back surface within the scope of the present disclosure can refer to the surface facing away from the display device.

In one configuration, provision can be made for the image capturing device to comprise a first camera and a second camera, wherein the first camera is configured to capture first image data from a first viewpoint and the second camera is configured to capture second image data from a second viewpoint; and wherein the computing unit is configured to determine the three-dimensional shape of the lens on the basis of the first and second image data. As an alternative to the use of two cameras, the first and second image data can also be captured by means of one camera at different positions. A displacement device or positioning device can be provided to move the camera between the first and the second position.

In an optional development, the first camera and the second camera can be arranged at an angle with respect to one another such that the test structure can be captured from the first angle by the first camera and from the second angle by the second camera.

The lens is a spectacle lens and the optical effect of the spectacle lens is calculated for a given wearing position of a user. One advantage can consist of the fact that, in particular, the optical effect can also be calculated retrospectively for any given specified or desired wearing position of the user. Here, the wearing position could also differ significantly from the measurement position, in which the image data are captured. The computing unit can be configured to calculate the optical effect of the spectacle lens for a specified wearing position of a user, which differs from a measurement position in which the image data are captured.

In particular, there can be a user-specific adaptation and a flexible calculation of used values. By contrast, conventional lensmeters provide no individualized statement for the user.

In one configuration, provision can be made for the computing unit to be configured to iteratively determine the three-dimensional shape of the lens by means of an integration method.

In a further configuration, provision can be made for the computing unit to be configured to determine the three-dimensional shape of the lens on the basis of tracing back the light beams entering the image capturing device. In particular, the light beams entering the image capturing device can be traced back to known original locations of the test structure displayed on the display device. In particular, the relative position of the display device and the positions or viewpoints, from which the image data are captured, are known. Optionally, the relative positions can be ascertained on the basis of the above-described camera calibration by means of changes in distance or height. By way of example, methods such as a back propagation or inverse ray tracing can be used to determine the three-dimensional shape of the lens. In simple terms, a surface reconstruction of the lens to be measured can be implemented on the basis of the comparison of an intended position and an actual position of one or more elements of the test structure in the captured image.

In one configuration, determining the three-dimensional shape of the lens can comprise a division of a front and/or back surface of the lens into surface elements and a determination of an alignment of the surface element, in particular a determination of surface normals of the surface elements. In particular, this determination can be undertaken on the basis of tracing back the light beams entering into the image capturing device. Expressed differently, an alignment of the surface can be determined for individual surface elements (for each individual surface element). By way of example, surface normals can be calculated for individual sections or surface elements.

In a development, the computing unit can be embodied to determine a three-dimensional shape of a front surface and/or a back surface of the lens on the basis of the alignment of the surface elements. A surface of the lens, for example the front or back surface, can be composed of individual surface elements. Typically, the surface is composed in such a way that no (significant) jumps arise between adjacent elements.

In one configuration, the computing unit can be configured to determine the three-dimensional shape of the lens taking into account the boundary condition that a front surface or a back surface of the lens is a parameterizable area, in particular a plane, sphere, torus or a section thereof. An advantage consists in a faster calculation and/or greater accuracy since the parameter space is reduced by specifying boundary conditions.

In one configuration, provision can be made for the computing unit to be configured to determine the three-dimensional shape of the lens further taking account of one or more known contact point(s) of the lens. As an alternative or in addition thereto, provision can be made for the computing unit to be configured to determine the three-dimensional shape of the lens taking account of a boundary condition, wherein the boundary condition is determined by reading information about the lens to be measured, in particular by reading a marking or a code on the lens. Once again, advantages can consist in the faster and/or more accurate calculation since the degrees of freedom are reduced further. It is understood that a plurality of known contact points or a lens glass holder or a spectacle holder can also be taken into account. By way of example, an engraving, a marker relating to a curvature, a material or a refractive index, can be read as a code on a lens and can be taken into account in the calculation.

In an exemplary configuration, which may assist with the understanding of the disclosure, provision can be made for the computing unit to be further configured to determine a refractive index, in particular to determine a spatial refractive index distribution, of the lens to be measured. A lens or spectacle lens with one refractive index can be considered to be a special case. Typically, the refractive index is constant in at least one portion. Further, a spatial refractive index distribution of a so-called GRIN (GRaded-INdex) lens can be determined. The inventors have recognized that the proposed solution can serve not only to capture a shape but also to determine the refractive index, i.e., to measure the interior of a transparent body. By way of example, it is possible to determine an internal interface between regions with different refractive indices. Possible applications include, for example, multi-part lenses, lenses with materials that have different refractive indices, achromatic lenses, optical systems or objectives.

In one configuration, the apparatus can further comprise a height adjustment device, which is configured to vary a distance between the image capturing device and the display device. Further, the computing unit can be configured to determine, on the basis of image data captured from different distances between the image capturing device and the display device, a beam direction of the light beams captured by the image capturing device. Consequently, an association between pixel and beam direction can be established in a simple manner.

The advantages described in detail above for the first aspect of the disclosure apply accordingly to the further aspects of the disclosure.

It goes without saying that the aforementioned features and those yet to be explained below can be used not only in the combination specified in each case but also in other combinations or on their own, without departing from the scope of the present disclosure.

BRIEF DESCRIPTION OF THE DRAWINGS

The disclosure will now be described with reference to the drawings wherein.

DESCRIPTION OF EXEMPLARY EMBODIMENTS

Figure 1:
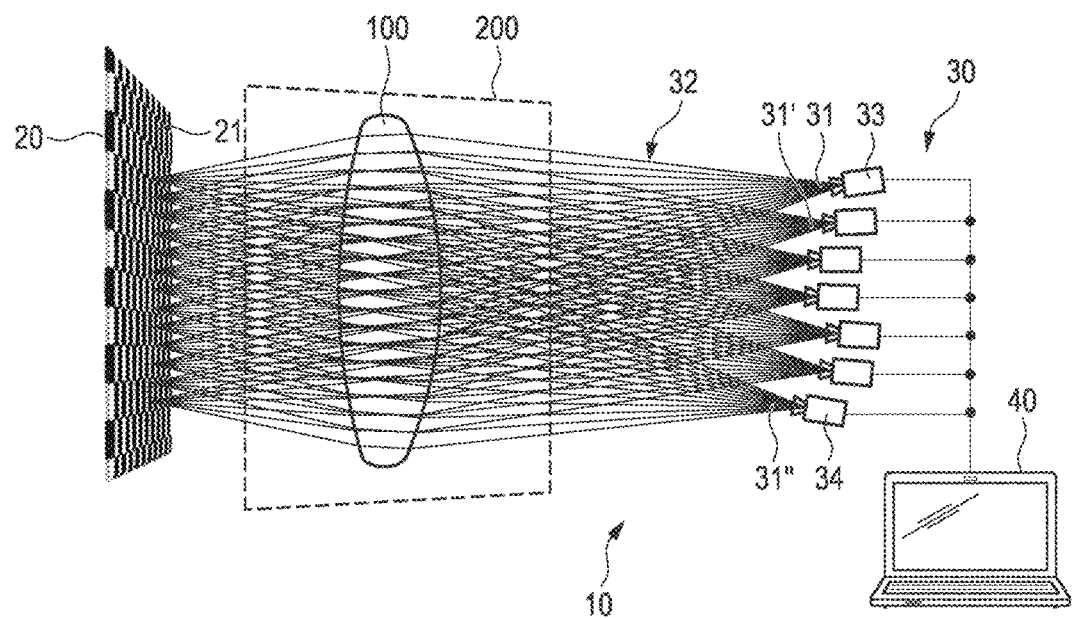
FIG. 1 shows an exemplary embodiment of an apparatus for measuring the optical effect of an optical lens arranged in a measurement volume.

The apparatus 10 shown in FIG. 1 serves to determine the optical effect of an optical lens 100, in particular a spectacle lens. The apparatus 10 comprises a display device 20, which is configured to display a test structure 21. By way of example, this could be a screen or display and to be able to display different test structures.

The apparatus 10 further comprises an image capturing device 30 which is configured to capture image data of the test structure 21 from a plurality of viewpoints 31, 31', 31" by way of imaging beam paths 32 which pass through the lens 100. On the one hand, the imaging beam paths from the various viewpoints could be recorded successively by one camera, which is successively arranged at the various positions. However, a plurality of cameras are typically provided in order to capture the image data in parallel. It is understood that mixed forms may also be provided. By way of example, an image capturing device 30 can comprise a first camera 33 and a second camera 34, wherein the first camera 33 is configured to capture first image data from a first viewpoint 33 and the second camera 34 is configured to capture second image data from a second viewpoint 33". The measurement volume 200 is located between the test structure 21, which is displayable on the display device 20, and the image capturing device 30.

The apparatus 10 further comprises a computing unit 40. By way of example, the computing unit 40 can be a computer, a microcontroller, an FPGA or the like. The computing unit 40 is configured to determine a three-dimensional shape of the lens 100 on the basis of the image data; and to calculate an optical effect of the lens 100 on the basis of the three-dimensional shape. Expressed differently, a two-stage procedure is proposed, in which the three-dimensional shape of the lens is initially determined and only then is the optical effect of the lens calculated from its three-dimensional shape.

This approach as per the present disclosure should be explained in more detail below with reference to FIGS. 2 to 6.

Figure 2:
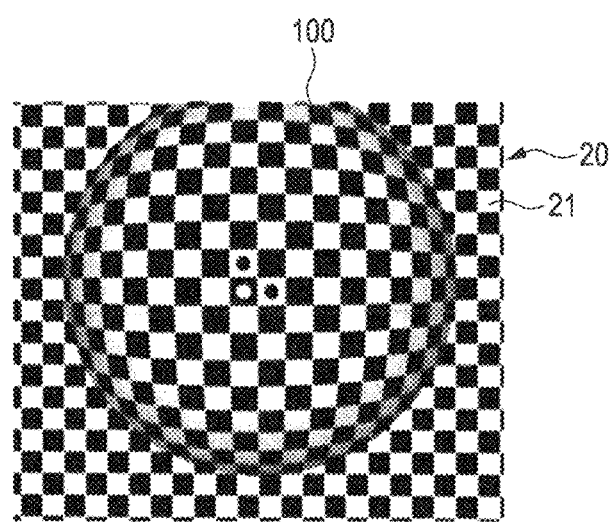
FIG. 2 shows an exemplary embodiment of a test structure recorded through a lens.

FIG. 2 shows a plan view of a test structure 21 of a display device 20 recorded through a lens 100. By way of example, this can be the test structure 21 as per FIG. 1, recorded by the camera 33 through the lens 100. The test structure 21 is reproduced in distorted fashion as a result of the lens 100. Conclusions about the optical effect of the lens 100 can already be drawn from such a deflection of the beams. However, it is only possible to make a statement about the effect of the lens 100 as a whole.

Figure 3:
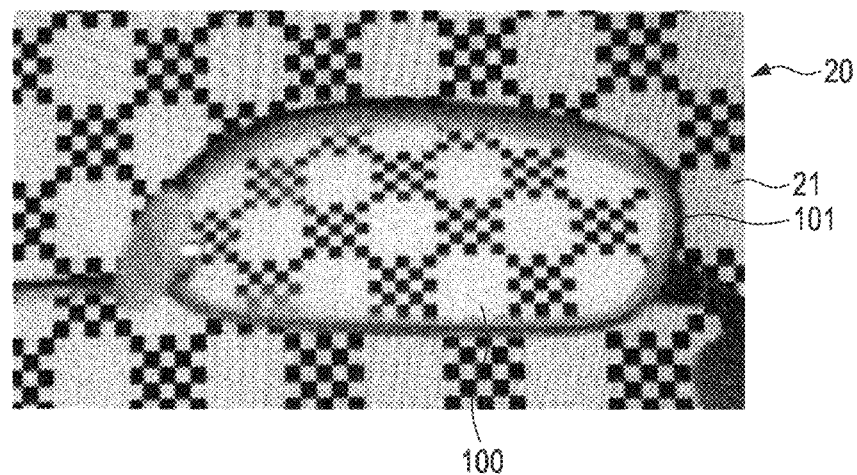
FIG. 3 shows an exemplary embodiment of a test structure recorded through a tilted spectacle lens.

FIG. 3 shows a further exemplary image, which has been recorded by a camera. However, in this case, the spectacles 101 with the optical lens 100 are arranged with a large tilt in the measurement region, and so the beam deflection caused by the optical lens 100 only reproduces the actual optical effect in a wearing position with limited accuracy.

Figure 4:
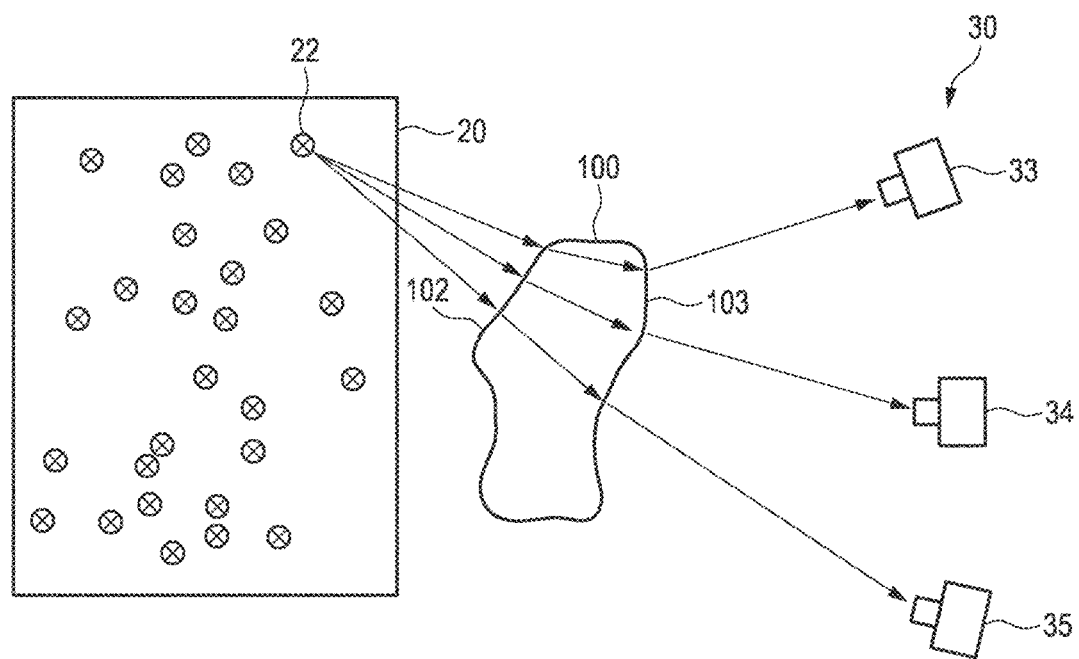
FIG. 4 shows an illustration of beam paths through a transparent object.

FIG. 4 shows an exemplary illustration of beam paths through a transparent object such as a lens 100. The origin of the beam paths is a defined point 22 on the display device 21. The beam paths emanating from the defined point 22 enter the lens 101 at the surface 102 and emerge from the lens at the surface 103. Consequently, they pass through the lens 100. The light beams are refracted both at the entry surface 102 and at the exit surface 103. A different optical effect may arise, depending on the relative spatial position or orientation of the lens 100 with respect to the display device 20 and the image capturing device 30.

The inventors have recognized that such uncertainty or ambiguity of the optical effect can be resolved by virtue of recording the test structure from a plurality of viewpoints and consequently capturing a multiplicity of imaging beam paths (see also FIG. 1), from which, in turn, the optical properties of an interposed lens can be determined. Expressed differently, a system of equations with a multiplicity of equations can be set up for the imaging beam paths, which equations each establish an association between imaging beams, which pass through the lens 100 and enter the image capturing device from a plurality of viewpoints, and the known origins thereof on the display device 20. From this, it is possible, in turn, to determine the three-dimensional shape of the lens 100 and also, optionally, its refractive index or a brake-force distribution within the lens as well.

Figure 5:
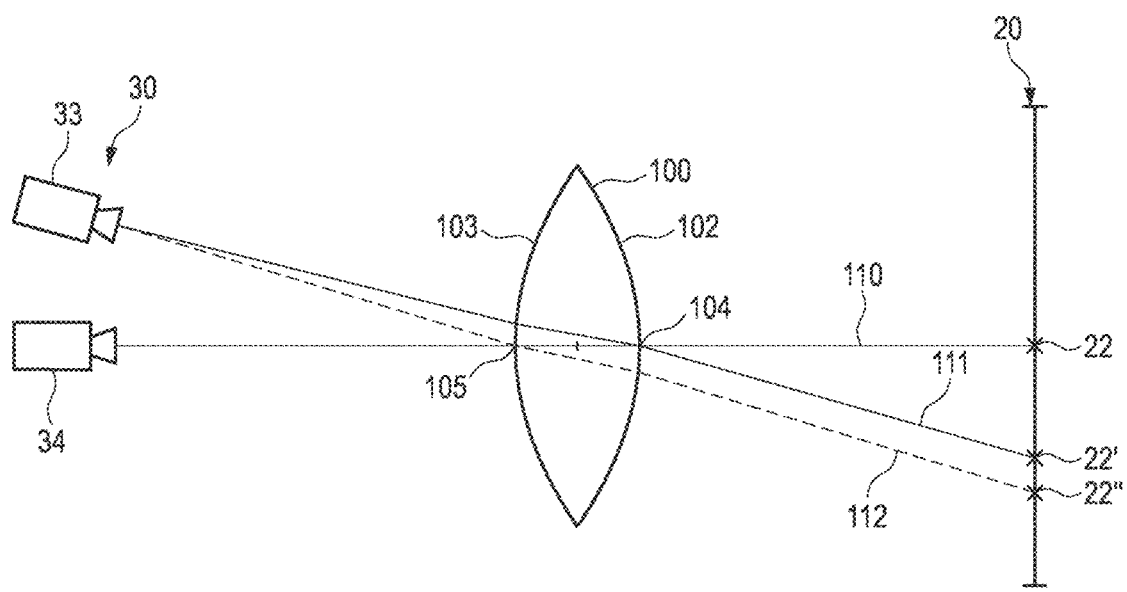
FIG. 5 shows an illustration of beam paths through a lens.

A simplified example of beam paths through a lens 100 is reproduced in FIG. 5. The image point 22 on the display device 20 is captured by the camera 34. The beam path 110 enters the lens at the point 104 on the front side 102 of the lens 100 and emerges from the lens at the point 106 on the back surface 103 of the lens. In simple terms, there is therefore an equation with two unknowns, the entry point 104 and the exit point 105 including the spatial orientation of the surface at these points, in the case of a measurement with only one camera. By virtue of the image capturing device 30 recording the test structure from further viewpoints, as indicated by the further camera 33, it is possible to capture further beam paths 111 and 112. In the case of the beam path 111, an exit point 104 coincides with the beam path 110 of the camera 34. In the case of the beam path 112, an entry point 105 coincides with the beam path 110 of the camera 34. Consequently, it is possible to set up a plurality of equations, from which it is possible to determine the properties of the lens 100 arranged between the display device 20 and the image capturing device 30.

Figure 6:
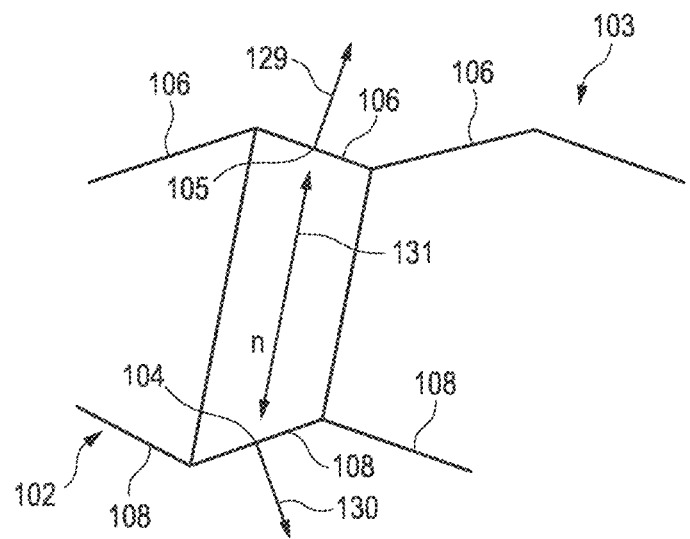
FIG. 6 shows a lens composed of parameterizable surface elements.

To this end, the computing unit can be configured to model the lens 100, typically as a composed surface made of parameterizable surface elements, as shown in FIG. 6 in exemplary fashion. An orientation of the surface elements 106, 107 of the front and back surface 102, 103 can be determined from the deflection of the beams at the points 104 and 105. Optionally, a further division can be undertaken within the lens 100. By way of example, further interfaces can be determined within the lens 100. Optionally, the computing unit can further be embodied to determine a refractive index of the lens 100 or else spatial refractive index distribution of the lens.

Optionally, the apparatus can be embodied as an apparatus for measuring a spatial refractive index distribution of an optical lens arranged in a measurement volume. To this end, provision can typically be made of an interface which is configured to receive lens geometry data, which describe a three-dimensional shape of the lens. In this case, the shape of the lens need not be calculated; instead, it can serve as an input parameter for calculating the spatial refractive index distribution of the lens on the basis of the image data and the lens geometry data.

Referring to FIG. 5 and FIG. 6, the computing unit can be configured to determine three-dimensional shape of the lens on the basis of tracing back the light beams entering the image capturing device. The directions from which the light beams 110, 111, 112 enter the cameras 33, 34 of the image capturing device are known. To this end, the image capturing device, as still described below, can be calibrated. Consequently, the entering beams can be traced back proceeding from the respective camera 33, 34. The lens 100 is located in the beam path between the image capturing device or the respective cameras (with a known position) and the test structure (with a known position). Proceeding from a model of the lens 100, this model can successively be parameterized by the computing unit in such a way that the (known) test structure is imaged by the model of the lens 100 in such a way that the image data captured by the image capturing device arise. For the parameterization, it is possible, in particular, to adapt the alignments of the surface elements, represented here by the surface normals 129, 130, forming the lens surface and vary a distance 131 between the surface elements, and it is optionally possible to vary a refractive index n or a refractive index distribution within the lens.

Figure 7:
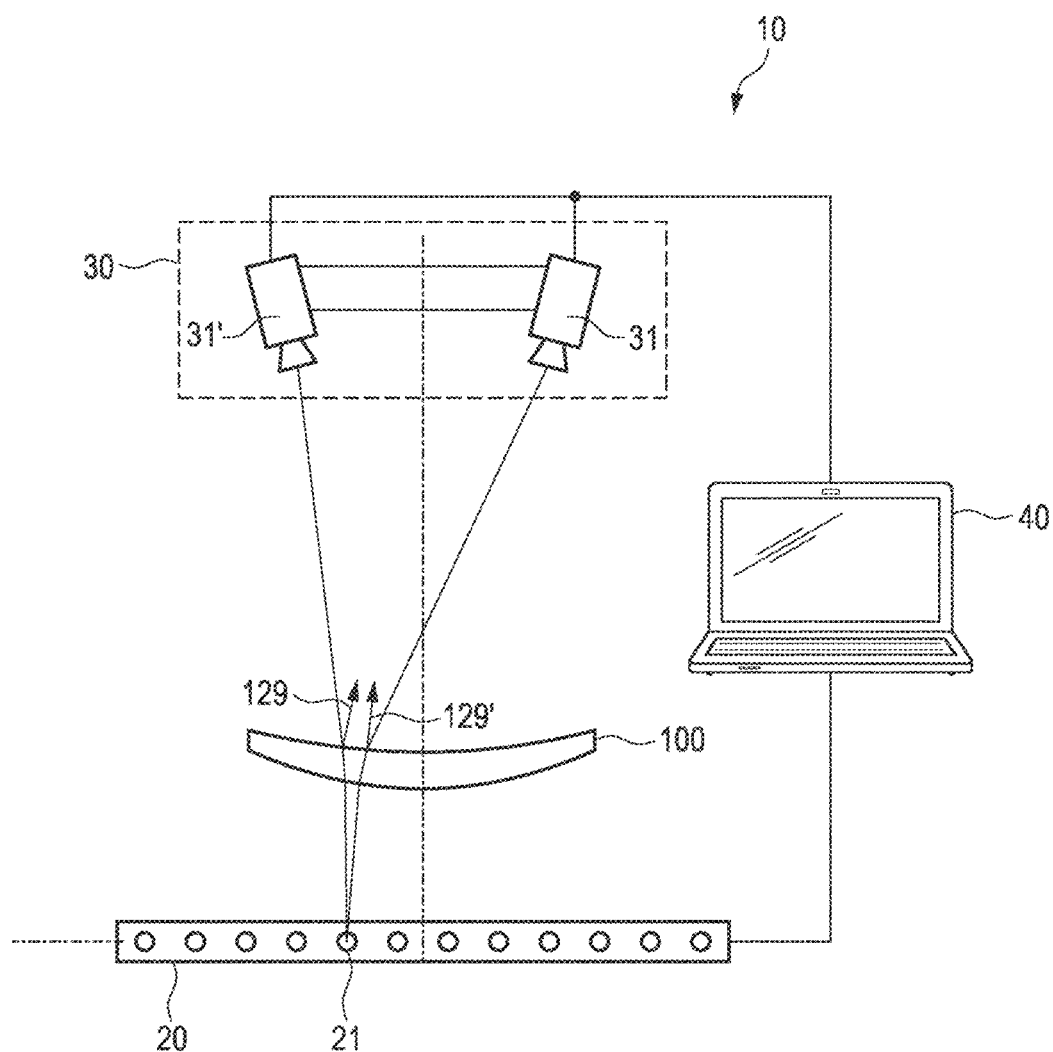
FIG. 7 shows a schematic illustration of an apparatus for measuring the optical effect of an optical lens arranged in a measurement volume.
Figure 8:
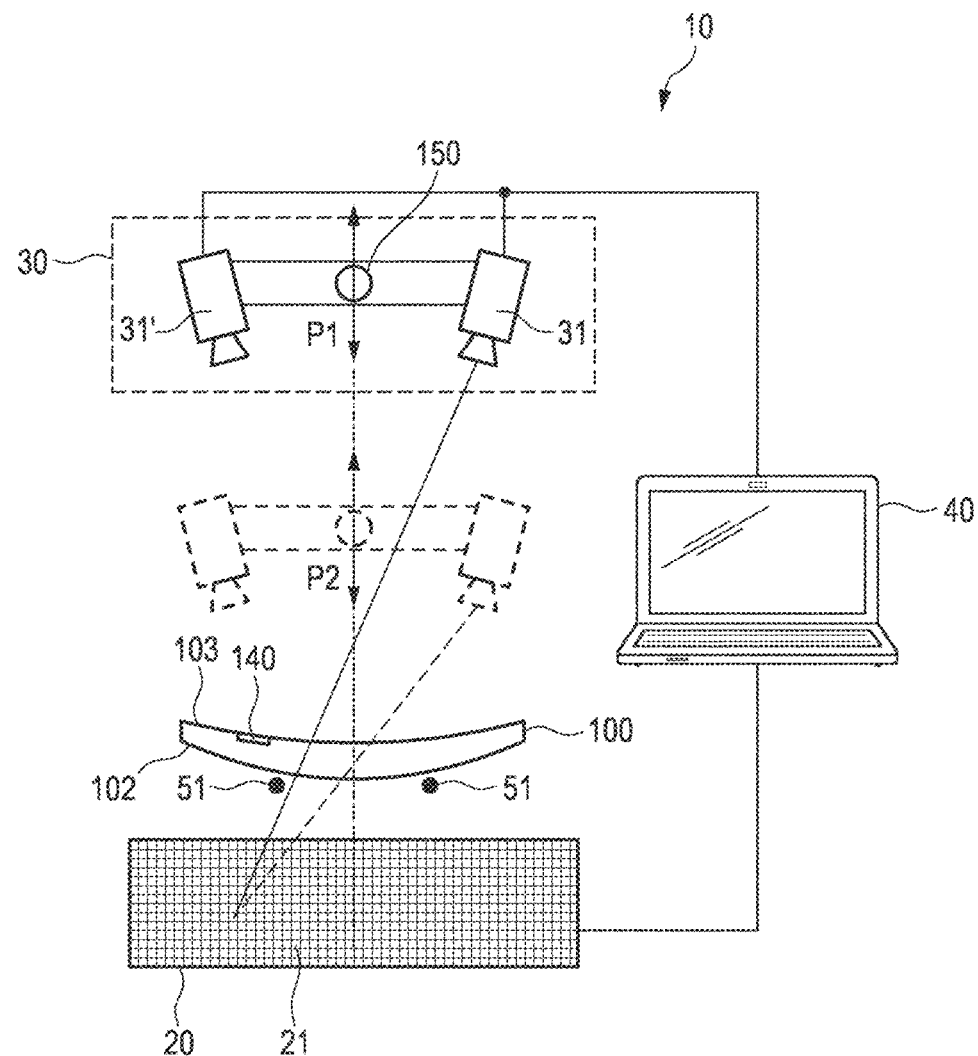
FIG. 8 shows a further exemplary embodiment of an apparatus for measuring the optical effect of an optical lens arranged in a measurement volume.

FIG. 7 and FIG. 8 show further exemplary embodiments of an apparatus 10 for measuring the optical effect of an optical lens 100 arranged in a measurement volume. Corresponding assemblies are denoted by the same reference sign and not explained again in detail in order to avoid repetition.

FIG. 8 shows an exemplary embodiment in which the image capturing device 30 comprises two cameras 30, 31'. The cameras see a pattern or a test structure 21 from different viewing angles. The computing unit is embodied to reconstruct the test object 4 from the corresponding image data. To this end, it is possible to determine a gradient field from the surface elements or from the normals 129, 129', as explained in FIGS. 5 and 6.

Light from defined sources at defined origins of the test structure 21 passes through the lens 100 and is captured by the image capturing device 30 from different viewing angles by means of a calibrated camera system. The refractive surfaces of the body are reconstructed from the images arising.

The principle works with one camera, two cameras or more cameras. Two cameras are used in an exemplary embodiment, as a good cost/use ratio can be obtained in this case. Even more cameras can be used to further increase the accuracy.

The image capturing device 30 or the cameras 31, 31' is/are calibrated in such a way that a function is known, by means of which a unique chief light ray (camera ray) can be derived in 3D for each sensor coordinate from the origin and direction. This calibration can be carried out according to the related art. Alternatively, a known optical design of the camera and/or of an employed objective can be included in the model of the camera instead of the above-described camera calibration.

By way of example, the display device 20 can have self-luminous sources, such as light-emitting diodes arranged in an array, a TFT or LED display, a 3D display, laser sources, a polarization display, or else a collimated, selectively structured illumination unit. Light can also be shone on the display apparatus. By way of example, a display apparatus on which light is shone may have test charts (e.g., a point pattern or checker pattern), an in particular regular 3D pattern, an unknown feature-rich flat image (wherein positions can be estimated during the operation) or else an unknown feature-rich 3D scene (positions are estimated during the optimization).

The computing unit 40 can use further information for determining the three-dimensional shape. The reconstruction of the three-dimensional shape may in particular also be based on the known viewpoints or positions of the camera, from which the image data are captured, and a known position of the test structure. In the present example, the image data can be locations of the imaging of light beams, entering the cameras, on the camera detectors. The light beams entering the image capturing device can be calculated from the image data and the known viewpoints. A calibration of the image capturing device can serve as a basis for this.

Optionally, the computing unit 40 can further be configured to determine the three-dimensional shape of the lens taking account of one or more boundary conditions. By way of example, a contact point or stop 51 may be predetermined. The relative position of the lens 100 is known at this point and can be taken into account when determining the three-dimensional shape of the lens. Further, information such as the shape of a front and/or back surface of the lens, a refractive index or material, etc., may be predetermined. Optionally, the apparatus can be embodied to read information present on the lens, for example in the form of an engraving or a marker 140, and take this information into account when determining the three-dimensional shape and/or when calculating the optical effect.

A particularly advantageous application of the present disclosure lies in the measurement of spectacle lenses, in particular the measurement of progressive spectacle lenses—also known as varifocal spectacle lenses. Simpler spectacle lenses such as spherical, aspherical, toric or prismatic lenses can, however, likewise be measured using the apparatus proposed.

Optionally, the computing unit can be configured to calculate an ISO vertex power or a vertex power in a specified measuring appliance configuration in order to provide comparable data. By providing wearer-specific data, such as the distance of a pupil from the spectacle lens (vertex distance) and its relative position (e.g., face form angle or "as worn" pantoscopic angle), it is possible to calculate use vertex powers.

Optionally, a plurality of test objects can be measured simultaneously in the measurement space. In the case where a pair of spectacles with a left and a right spectacle lens is measured, the computing unit can be further embodied to determine a position and relative position of the spectacle lenses with respect to one another. From this, it is possible to calculate further information, such as the distance of the optical channels for example. A transparent body with zones of different effects can also be provided as a plurality of test objects. By way of example, this can be a pair of spectacles with two lenses or a lens with a plurality of zones—bifocal lens, trifocal lens or multifocal lens.

Figure 9:
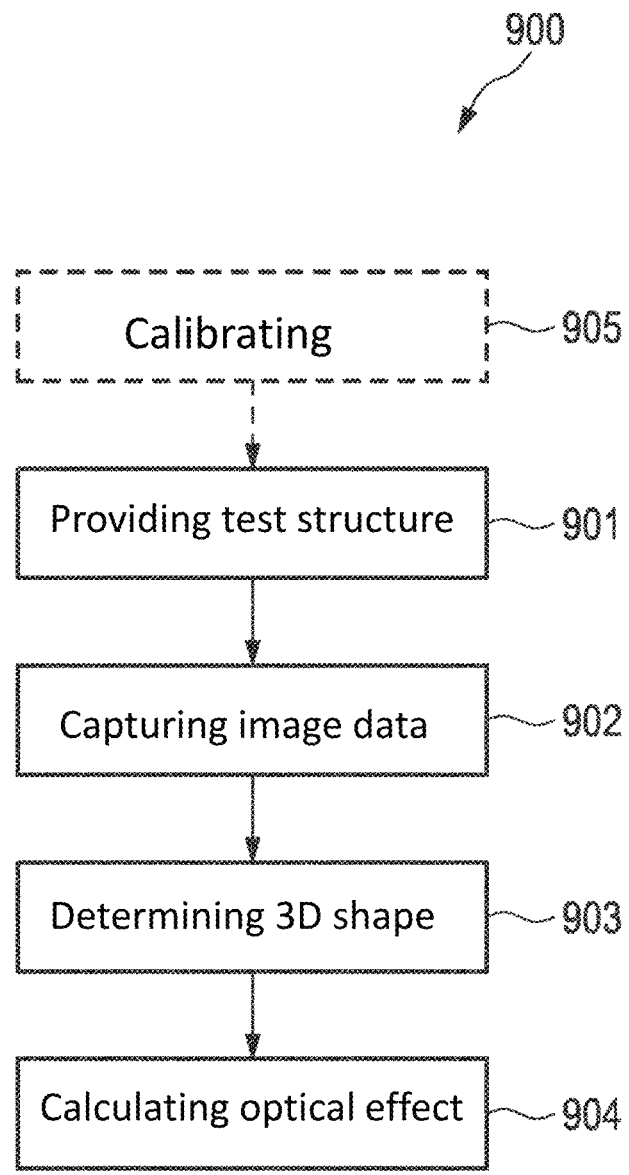
FIG. 9 shows a flow chart of a configuration of a method for measuring the optical effect of an optical lens arranged in a measurement volume.

FIG. 9 shows a flow chart of a method 900 for measuring the optical effect of an optical lens, in particular a spectacle lens, arranged in a measurement volume, including the steps set forth below. In a first step 901, a test structure is provided for display on a display device. In a second step 902, image data of the test structure are captured from a plurality of viewpoints by way of imaging beam paths that pass through the lens. In a third step 903, a three-dimensional shape of the lens is determined on the basis of image data (and the known positions of the viewpoints and the display device relative to one another). In a fourth step 904, an optical effect of the lens is calculated on the basis of its three-dimensional shape. The calculation can be implemented for any usage situation. Consequently, the computing unit can be configured to calculate a first optical effect, corresponding to an ISO vertex power, and a second optical effect, corresponding to a usage situation by a user.

Optionally, the measuring method can be preceded by step 905 for calibrating the apparatus.

A corresponding method for calibrating the apparatus may, in turn, include the following steps: In a first calibration step, a test structure is provided on the display device. In a second calibration step, a first distance is set between the image capturing device and the display device and image data of the test structure are captured from the first distance by means of the image capturing device.

As shown in FIG. 8, provision can be made of a height adjustment device 150, which is configured to vary a distance between the image capturing device and the display device. In this context, the computing unit can be further configured to determine, on the basis of image data captured from different distances between the image capturing device and the display device, a beam direction of the light beams captured by the image capturing device.

In a further step of the method for calibrating the apparatus, a second distance can be set between the image capturing device and the display device and image data of the test structure are captured from the second distance by means of the image capturing device. From this, a direction of incident light beams, captured by the image capturing device, and corresponding image points in the image data can be determined in a further step.

Figure 10:
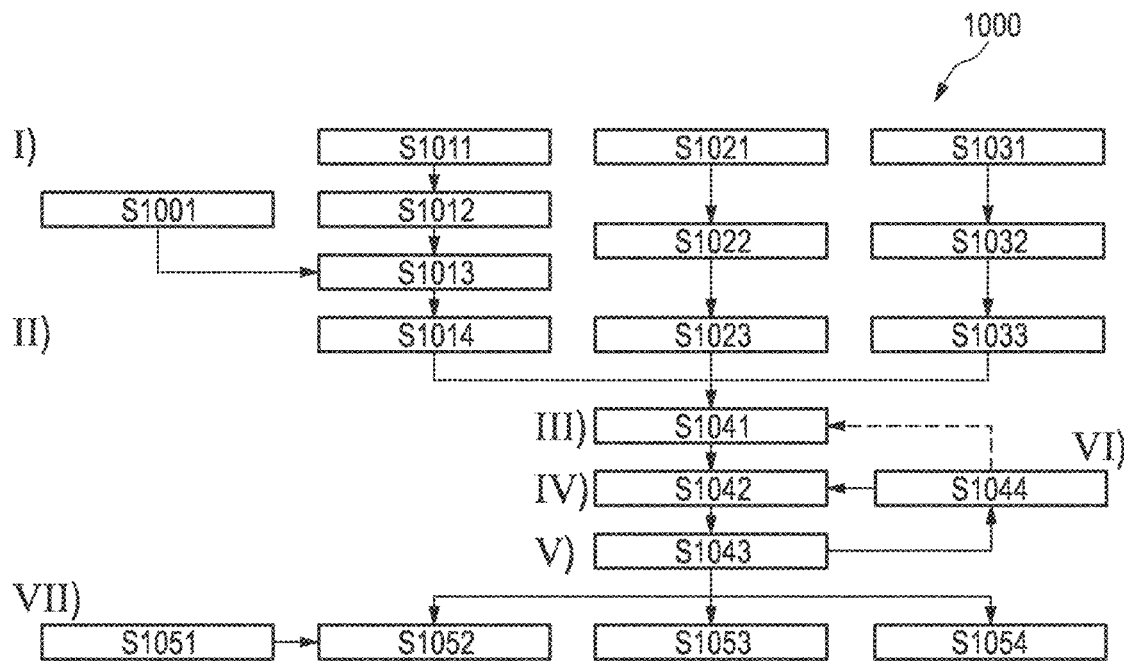
FIG. 10 shows a detailed flowchart of a configuration of such a method.

FIG. 10 shows a detailed flow chart of an exemplary embodiment of a method 1000 for measuring the optical effect of a lens arranged in a measurement volume.

In a first step S1011, a test structure is displayed on the display device. By way of example, this can be an entire point or stripe pattern. In a further step S1012, image data of the test structure are captured by the image capturing device. In step S1013, it is possible to determine positions of features of the test structure, for example the positions of pattern points in the image data (corresponding to positions on a detector surface of the image capturing device). Here, there can be a camera calibration step S1001, as explained above or described in detail in FIG. 11, for example. In step S1014, it is then possible to determine the light beams incident in the image capturing device or the directions thereof. The light beams incident in the camera can be determined as a 3D vector from the camera images of the displayed pattern, as observed through the lens to be measured.

In a step S1021, a complete or partial pattern of a test structure can be displayed on the display device. In a further step S1022, image data of the test structure are captured by the image capturing device. In step S1023, pattern points can be associated with image points in the image data. In particular, it is possible to provide a sequence of different test patterns in order to resolve a possible ambiguity when associating pattern points with image points in the image data. Expressed differently, luminous spots in the image data captured by the image capturing device can be assigned to a position of the luminous points on the display device, and hence also to the calculated light beams, which were incident in the image capturing device. As an alternative or in addition thereto, the computing unit can be configured to determine neighborhood relationships from an overall pattern of a test structure.

In a step S1031, a planar illumination can be provided on the display device. By way of example, all pixels of the display device could display "white". As a consequence, a contour of the lens could stand out and a contour of the lens can be determined in step S1032. In a step S1033, a relative position and dimensions of the lens can be determined on the basis of the captured contour. Expressed differently, a relative position of the lens in the measurement volume can be determined in a simple manner.

In step S1041, there can be a calculation of a "best fitting" parameterizable lens. Typically, a "best fitting" parameterizable lens, which could lie in the measurement volume of the appliance, can be ascertained by back propagation of the camera light beams. A parameterizable lens is understood to mean a lens that can be described by few parameters such as radius, thickness or the refractive index. These include spherical and toric lenses, for example. Toric lenses are a general compromise, which may be applied here. In a more specific exemplary embodiment, it may be sufficient to define individual "toric zones" on the lens and only describe the spectacle lens there. By way of example, a first of these zones could be a "far region" of a progressive lens. By way of example, a second of these zones could be a "near region" of a progressive lens. In addition to the location of the lens or the individual surfaces, further parameters could be the radii, the thickness and the refractive index.

In step S1042, a "best fitting" gradient surface of the front and/or back surface of the lens can be determined by inverse ray tracing of the camera rays. Consequently, a surface of the "best fitting" parameterizable lens determined in step S1041 can be described as a gradient surface and the gradients at the locations of the beam passage can be varied in such a way that the positions of the luminous points on the display device are impinged perfectly by back propagation of the camera rays. In simple terms, the three-dimensional shape of the lens is therefore adapted in such a way that the light beams received by the image capturing device and the associated beam sources fit together on the display device.

In step S1043, a front and/or back surface of the lens can be obtained by integration from the gradient surface. Expressed differently, a (continuous) new surface is determined from a piecewise gradient surface or a gradient surface determined for surface elements. Here, this could be the front surface or the back surface of the lens.

According to step S1044, steps S1042 and S1043 can be repeated iteratively. By way of example, the steps could be repeated until a quality criterion has been satisfied. Optionally, if a sufficient quality cannot be reached, step S1041 can also be included in the iteration loop, in order to take account of alternative lens geometries. A three-dimensional shape of the lens can be available as a result of the iteration.

In a further exemplary embodiment, which may assist with the understanding of the disclosure, a shape of the lens can be predetermined and, instead, a spatial refractive index distribution within the lens can be iteratively determined in analog fashion.

One or more variables can be subsequently determined from the determined three-dimensional shape (optionally including the refractive index). A use value, in particular a user-specific use value, can be calculated in step S1052. To this end, wearer-specific data, such as a distance between cornea and apex, can be provided in step S1051. An ISO vertex power can be determined in step S1053. A vertex power in an appliance configuration can be determined in step S1054.

If a plurality of lenses or spectacle lenses were arranged in the measurement volume at the same time, it is optionally possible to determine additional parameters, such as the spacing of the progression channels.

It is understood that the aforementioned steps can be carried out by the computing unit and that the latter can be configured accordingly for the purposes of carrying out the steps.

Figure 11:
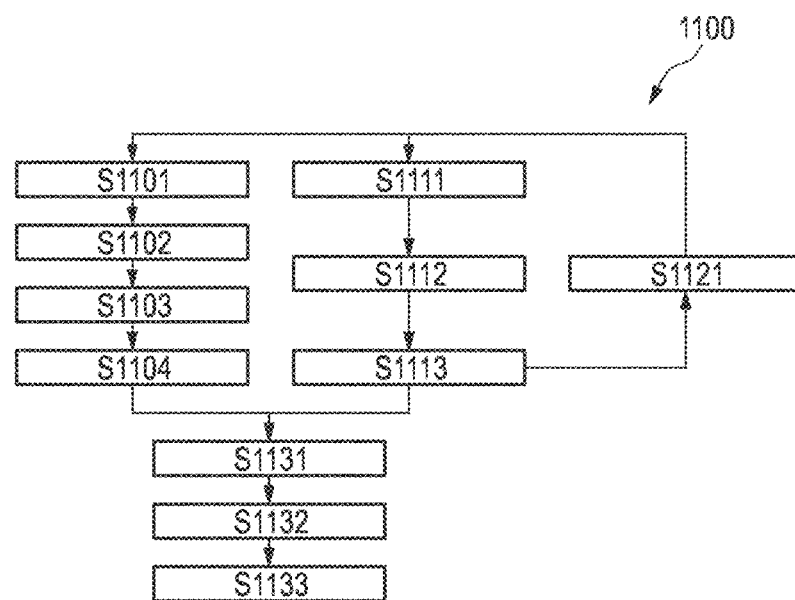
FIG. 11 shows a flowchart of an exemplary embodiment of a calibration method.

FIG. 11 shows a flow chart of an exemplary embodiment of a method 1100 for calibrating an apparatus for measuring individual data of an optical lens arranged in a measurement volume, which may assist with the understanding of the disclosure. The calibration can serve, in particular, to provide a set of functions, which assigns a beam direction such as a 3D vector to an image point—typically each image point—of the image data captured by the image capturing device, the 3D vector describing a beam direction or a light beam entering the image capturing device. Such a set of functions can have the following form:

$$\vec{r}(x, y) = \begin{pmatrix} x_0 \\ y_0 \\ 0 \end{pmatrix} + \alpha \begin{pmatrix} dx \\ dy \\ 1 \end{pmatrix}$$

where $(x_0, y_0, 0)$ describes a point of the light beam in a reference plane of the image capturing device, typically a point of the light beam in a reference plane in the lens system of a camera of the image capturing device, and $(dx, dy, 1)$ describes the direction vector of the incident beam. Consequently, the set of functions consists of four functions: $x_0(x,y)$, $y_0(x,y)$, $dx(x,y)$, and $dy(x,y)$, where x and y describe the pixel coordinates in image data of the image capturing device, a camera in this case.

Such a set of functions can be determined by virtue of a test structure, e.g., a point pattern, being displayed on the display device and being observed by the cameras of the image capturing device from different distances. For this purpose, the apparatus as illustrated in FIG. 8 in exemplary fashion can comprise a height adjustment device 150, which is configured to vary a distance between the image capturing device and the display device.

In the method shown in FIG. 11, steps S1101 to S1104 can respectively correspond to steps S1011 to S1014 in FIG. 10, which were described above. Steps S1111 to S1113 shown in FIG. 11 can each correspond to the above-described steps S1021 to S1023. However, a loop is provided, with a distance between the image capturing device and the display device being varied in step S1121. As shown in FIG. 8, a variation in the distance changes a direction of the incident light beams. The computing unit can be configured to determine a direction of the incident light beams on the basis of the image data captured at the first distance and the image data captured at the second distance. It is understood that this determination can further depend on a relative position between the display device and the image capturing device and on the variation of the distance.

As shown in FIG. 11, an interpolation of 3D light beams of a plurality of image points or pixels, typically for each image point or pixel, of the image capturing device can be undertaken in a step S1131. Subsequently, the variables $x_0$, $y_0$, dx, and dy can be determined for the image points in step S1132. In a next step S1133, a polynomial fit can be applied to the variables $x_0$, $y_0$, dx, and dy. As a result, this can be used to determine a set of functions which assigns a direction of an incident light beam to each image point of the image data captured by the image capturing device.

Optionally, a relative spatial position of a contact point 51, as illustrated in exemplary fashion in FIG. 8, can be determined in a manner analogous to the camera calibration. To this end, the display device 20 can be configured to display a single color background or a background with a constant brightness as a test structure. The image capturing device captures the display without an inserted lens. In this case, the contact points lead to shadow (e.g., circle in the case of contact spheres), which is captured by the image capturing device and contained in the image data. The computing unit can be embodied to determine a position of the contact points 51 on the basis of these image data. In turn, these can be used as boundary conditions when determining a three-dimensional shape of a lens. When observing a contact point by at least two cameras, its central point (the relative position) can be ascertained by an intersection of the camera rays. The position of the contact points can be used to assign to an algorithm for determining the shape of the spectacle lens an expected value for the position of the latter in the measurement volume. An advantage of this configuration consists in an improved accuracy.

It is understood that the explanations made above can apply accordingly to the exemplary embodiments below, and vice versa. To avoid repetition, further aspects, in particular, are intended to be discussed below. Features of the aforementioned exemplary embodiments and the exemplary embodiments below can advantageously be combined with one another.

Figure 12:
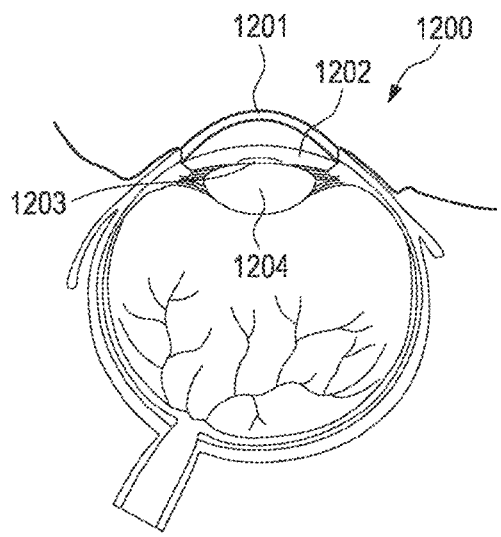
FIG. 12 shows a schematic illustration of an eye.
Figure 13:
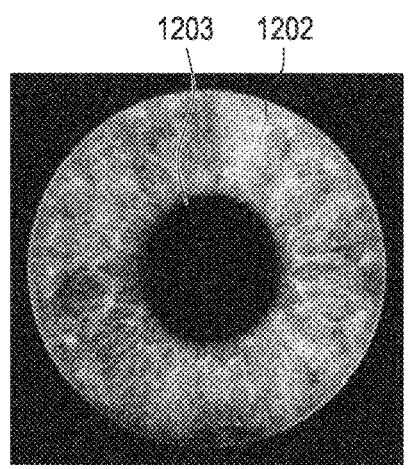
FIG. 13 shows an image representation of a plan view of the eye with an image representation of the iris.

The inventors have recognized that the concepts described herein can also be advantageously used for measuring the cornea. FIG. 12 shows a schematic sectional illustration of an eye 1200. The eye comprises a cornea 1201, an Iris 1202, a pupil 1203, and the lens 1204. FIG. 13 shows a plan view of the eye with an image representation of the iris 1202 and the pupil 1203. However, a substantial contribution to the refractive error does not come from the lens 1204 in this case, but from the cornea 1201. A substantial contribution to the refractive error of a subject can be due to corneal curvature. It would therefore be desirable to be able to objectively determine the shape of the cornea.

Figure 14:
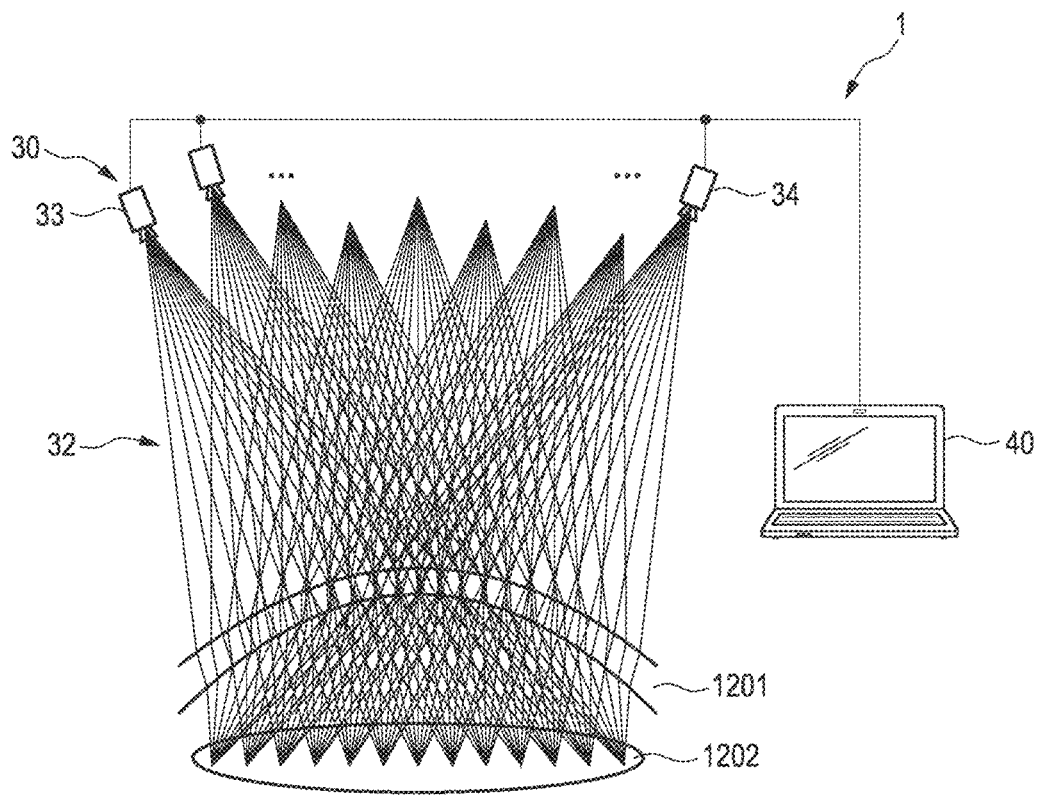
FIG. 14 shows a schematic illustration of an apparatus for measuring the cornea.

FIG. 14 shows a schematic illustration of an apparatus for measuring the cornea of a subject as per a further aspect of the present disclosure. The apparatus may comprise the following: an image capturing device (30), which is configured to capture image data of an iris (1202) of the subject from a plurality of (known) viewpoints by way of imaging beam paths (32) which pass through the cornea (1201); and a computing unit (40). The computing unit is configured to: provide a mathematical model of an anterior eye section of the subject including a mathematical model of the cornea and the iris; identify and register image features of the iris which are present in a plurality of images of the image data; determine deviations between actual positions of the image features of the iris in the images captured from the plurality of viewpoints and expected positions of the image features of the iris in the images captured from the plurality of viewpoints taking into account the mathematical model of the cornea and the relative position of the iris; adapt parameters of the mathematical model of the cornea in such a way that the deviations are minimized; and determine a measured variable of the cornea from the adapted mathematical model of the cornea.

The image capturing device 30 can again have the same or similar configuration as described for FIG. 1. The image capturing device captures image data of the iris 1202, with the beam paths passing through the cornea 1201. To capture the image data from different known viewpoints, a camera 33 can be successively positioned at different known positions. To this end, provision can be made of a positioning device (not shown). As an alternative or in addition thereto, provision can be made of a plurality of cameras 33, 34, which capture the image data in parallel. An advantage of the parallel capture consists of the eye of the user not moving between the various measurements.

The inventors have recognized that the cornea 1201 situated between the iris 1202 and the image capturing device 30 can also be calculated without knowledge about how the iris 1202 looks. The iris 1202 has an unknown structure or an unknown pattern. However, the iris 1202 is usually very structured. The inventors have recognized that a multiplicity of image features of the iris can be identified and subsequently evaluated in respect of their position in a plurality of images of the image data, which were recorded from different positions. To this end, a system of equations can be set up from the imaging beam paths 32 which are captured at the respective known positions; the shape of the cornea 1201 can be calculated therefrom.

Figure 15:
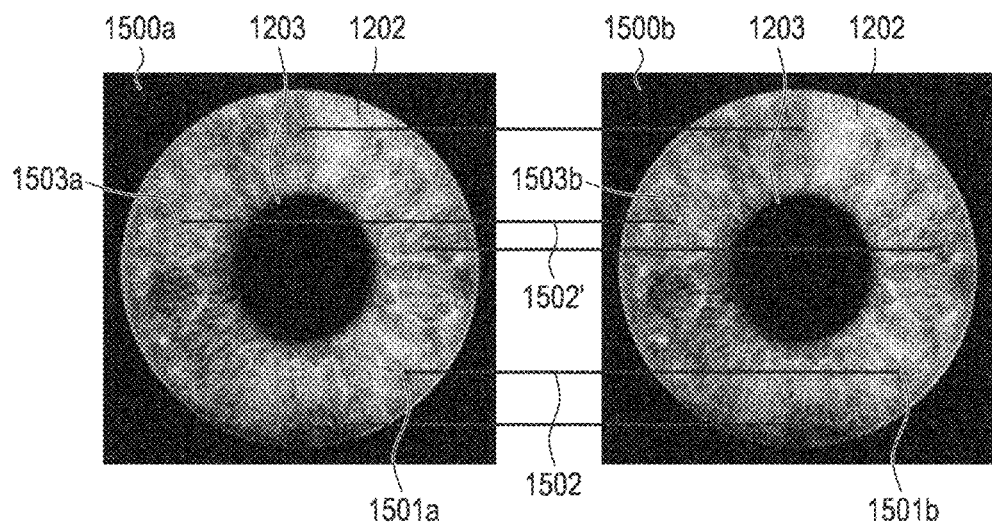
FIG. 15 shows the association or correlation of image features in images of the iris recorded from different viewpoints.
Figure 16:
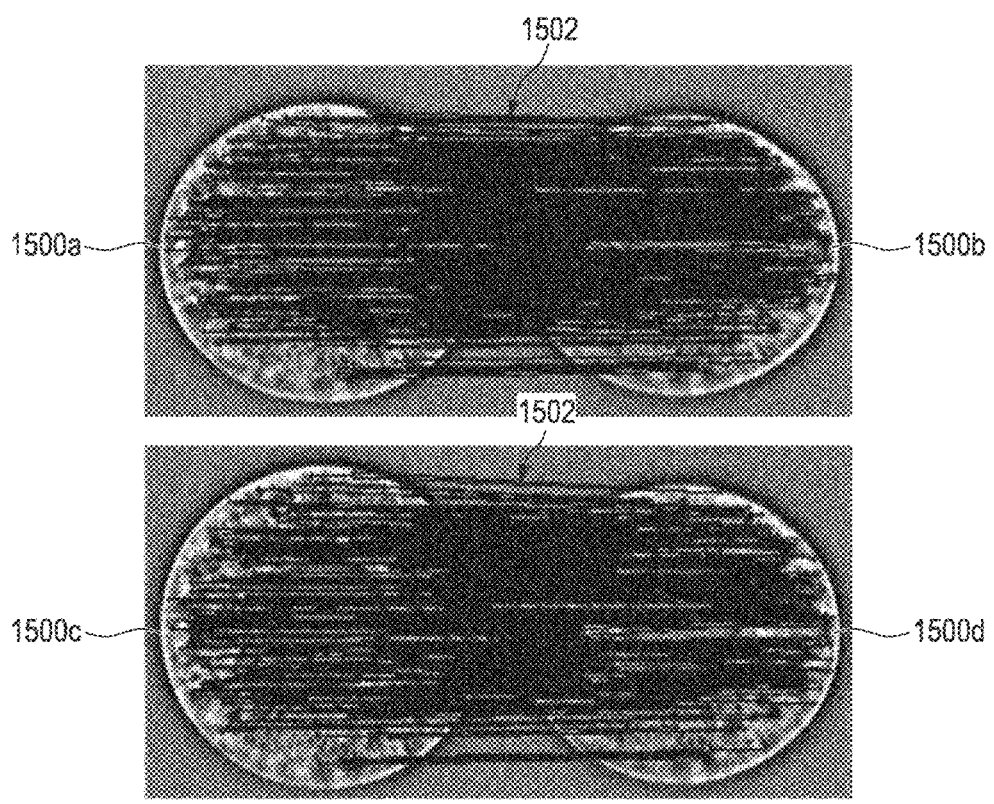
FIG. 16 shows a further correlation of image features.

FIG. 15 and FIG. 16 show the association or correlation of unknown image features in images of the iris recorded from different viewpoints. The left image in FIG. 15 shows a first image representation 1500a of the iris 1202—through the cornea—from a first position, for example recorded by the camera 33 in FIG. 14. The right image in FIG. 16 shows a second image representation 1500b of the iris 1202—through the cornea—from a second position, for example recorded by the camera 34 in FIG. 14. Since the iris is usually a very structured area, it is possible to determine a correlation 1502 between the same initial points 1501a and 1501b of the iris 1201. A further example of the corresponding points is specified by the reference signs 1503a and 1503b, linked by 1502'. Such an association 1500 can be undertaken for a multiplicity of images 1500a to 1500d and image points, as shown in FIG. 16.

On the basis of this correlation or association analysis, it is possible to reconstruct a multiplicity of beam paths, as shown in FIG. 14. As is evident from the shown beam paths 32, the light beams emanating from the same image point on the iris 1202 pass through the cornea 1201 at different points and are captured at different locations by the image capturing device 30. Should now the same starting point be identified in the image representations, it is possible to make statements about the cornea 1201, which is located between the starting point on the iris 1202 and the entry into the cameras 33, 34, as described above with reference to FIG. 14.

Figure 17:
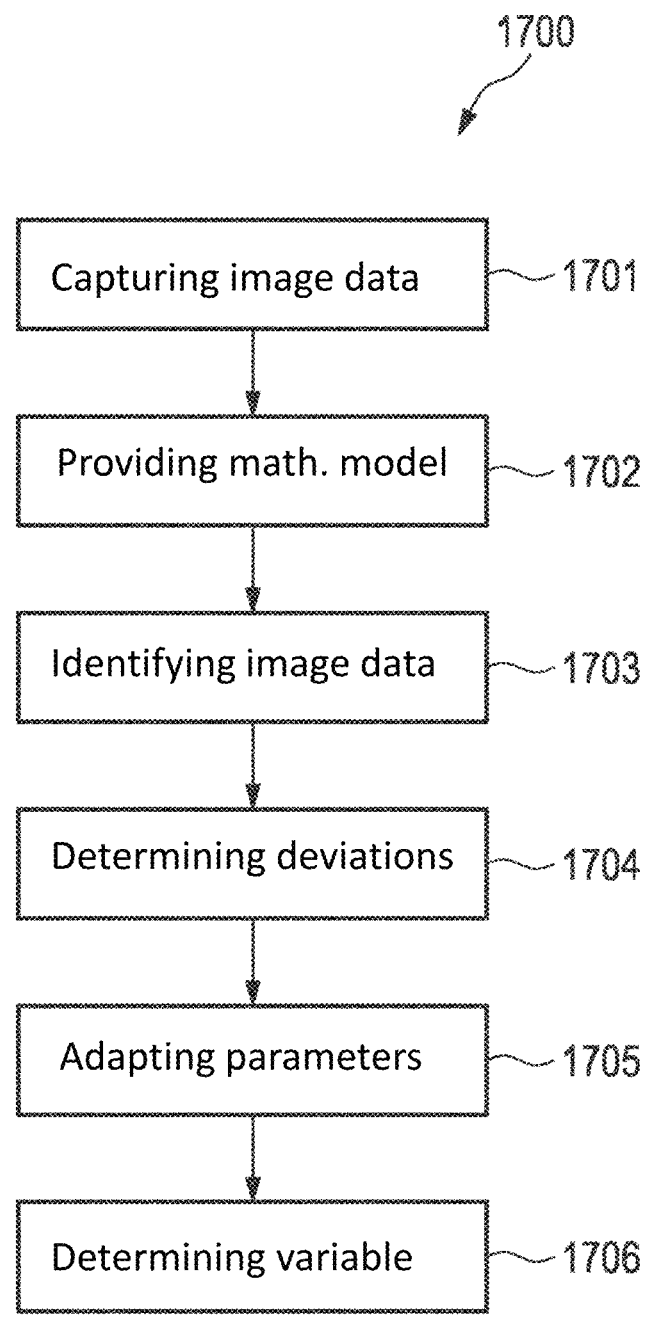
FIG. 17 shows a flowchart of an exemplary embodiment of a method for measuring the cornea.

FIG. 17 shows a flowchart of an exemplary embodiment of a method for measuring the cornea of a subject, which may assist with the understanding of the disclosure. The camera system can be calibrated in an optional preceding step. However, the manufacturer may have already carried out the calibration. In a first step 1701, image data of an iris of the subject can be captured from a plurality of viewpoints by way of imaging beam paths that pass through the cornea. In a second step 1702, a mathematical model of an anterior eye section of the subject with a mathematical model of the cornea (and the relative position of the iris with respect to the cornea) can be provided. In a third step 1703, image features of the iris which are present in a plurality of images (typically in all images) of the image data can be identified and registered (or assigned in the images). In a fourth step 1704, it is possible to determine deviations between the actual positions of the image features of the iris in the images captured from a plurality of viewpoints and the expected positions of the image features of the iris in the images captured from a plurality of viewpoints taking into account the mathematical model of the cornea and the relative position of the iris. In a fifth step 1705, parameters of the mathematical model of the cornea can be adapted in such a way that the deviations are minimized. Steps 1703 and 1704 can typically be repeated iteratively. In a sixth step, it is now possible to determine a measured variable of the cornea from the adapted mathematical model of the cornea. By way of example, a refractive power or an astigmatism can be evaluated.

In conclusion, the solutions disclosed herein can facilitate, in particular, a simplified contactless measurement of lens elements arranged in a measurement volume or else a contactless measurement of the cornea, in particular with a reduced impairment of a light-sensitive user, in the field of ophthalmic optics.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

The invention claimed is:

1. An apparatus for measuring an optical effect of a spectacle lens arranged in a measurement volume, the apparatus comprising:
   a display device configured to display a test structure;
   an image capturing device configured to capture image data of the test structure from a plurality of viewpoints along respective imaging beam paths passing through a spectacle lens; and
   a computing unit configured to:
      determine a three-dimensional shape of the spectacle lens on a basis of the image data; and
      calculate an optical effect of the spectacle lens on a basis of the three-dimensional shape of the spectacle lens for a specified wearing position of a user, which differs from a measurement position in which the image data are captured.

2. The apparatus as claimed in claim 1, wherein the image capturing device further comprises:
   a first camera configured to capture first image data from a first viewpoint; and
   a second camera configured to capture second image data from a second viewpoint,
   wherein the computing unit is configured to determine the three-dimensional shape of the spectacle lens on the basis of the first image data and the second image data.

3. The apparatus as claimed in claim 1, wherein the computing unit is configured to iteratively determine the three-dimensional shape of the spectacle lens with an integration method.

4. The apparatus as claimed in claim 1, wherein the computing unit is configured to determine the three-dimensional shape of the spectacle lens on a basis of back tracing the respective imaging beam paths entering the image capturing device.

5. The apparatus as claimed in claim 1, wherein the computing unit is configured to determine the three-dimensional shape of the spectacle lens by dividing at least one of a front surface or a back surface of the spectacle lens into surface elements and to determine an alignment of the surface elements.

6. The apparatus as claimed in claim 5, wherein the computing unit is configured to determine a three-dimensional shape of the front surface and the back surface of the spectacle lens on the basis of the alignment of the surface elements.

7. The apparatus as claimed in claim 1, wherein the computing unit is configured to determine the three-dimensional shape of the spectacle lens taking account of a boundary condition that a front surface or a back surface of the lens has a parameterizable area.

8. The apparatus as claimed in claim 7, wherein the parameterizable area includes a sphere, a section of the sphere, a torus, or a section of the torus.

9. The apparatus as claimed in claim 1, wherein the computing unit is further configured to determine the three-dimensional shape of the spectacle lens taking account of one or more known contact points of the spectacle lens.

10. The apparatus as claimed in claim 1, wherein the computing unit is configured to determine the three-dimensional shape of the spectacle lens taking account of a boundary condition, wherein the boundary condition is determined by reading information about the spectacle lens to be measured.

11. The apparatus as claimed in claim 10, wherein the boundary condition is determined by reading a code on the spectacle lens.

12. The apparatus as claimed in claim 1, wherein the computing unit is configured to determine a spatial refractive index distribution of the spectacle lens to be measured.

13. The apparatus as claimed in claim 1, further comprising:
   a height adjustment device configured to vary a distance between the image capturing device and the display device,
   wherein the computing unit is further configured to determine, on the basis of image data captured from different distances between the image capturing device and the display device, a beam direction of light beams captured by the image capturing device.

14. An apparatus for measuring an optical effect of a spectacle lens arranged in a measurement volume, the apparatus comprising:
   a display device configured to display a test structure;
   an image capturing device configured to capture image data of the test structure from a plurality of viewpoints along respective imaging beam paths passing through a spectacle lens; and
   a computing unit configured to:
      assign an expected value for a position of the spectacle lens in a measurement volume based on a position of one or more known contact points of the spectacle lens;

determine the three-dimensional shape of the spectacle lens; and calculate an optical effect of the spectacle lens on the basis of the three-dimensional shape of the spectacle lens.

15. An apparatus for measuring an optical effect of a spectacle lens arranged in a measurement volume, the apparatus comprising:

a display device configured to display a test structure;

an image capturing device configured to capture image data of the test structure from a plurality of viewpoints along respective imaging beam paths passing through a spectacle lens; and a computing unit configured to:
read a code on the spectacle lens containing information about a boundary condition;
determine a three-dimensional shape of the spectacle lens on a basis of the image data and the boundary condition; and
calculate an optical effect of the spectacle lens on the basis of the three-dimensional shape of the spectacle lens.

16. A method for measuring an optical effect of a spectacle lens arranged in a measurement volume, the method comprising:

providing a test structure for display on a display device;

capturing image data of the test structure from a plurality of viewpoints along respective imaging beam paths passing through a spectacle lens;

determining a three-dimensional shape of the spectacle lens on the basis of the image data; and calculating an optical effect of the spectacle lens on the basis of the three-dimensional shape of the spectacle lens for a specified wearing position of a user, which differs from a measurement position in which the image data are captured.

17. A method for measuring an optical effect of a spectacle lens arranged in a measurement volume, the method comprising:

providing a test structure for display on a display device;

capturing image data of the test structure from a plurality of viewpoints along respective imaging beam paths passing through a spectacle lens;

assigning an expected value for a position of the spectacle lens in the measurement volume to an algorithm based on a position of one or more known contact points of the spectacle lens;

determining a three-dimensional shape of the spectacle lens on the basis of image data taking account of the one or more known contact points of the spectacle lens; and calculating an optical effect of the spectacle lens on the basis of the three-dimensional shape of the spectacle lens.

18. A method for measuring an optical effect of a spectacle lens arranged in a measurement volume, the method comprising:

providing a test structure for display on a display device;

capturing image data of the test structure from a plurality of viewpoints along respective imaging beam paths passing through a spectacle lens;

reading a code on the spectacle lens containing information about a boundary condition;

determining a three-dimensional shape of the spectacle lens on a basis of the image data and the boundary condition; and calculating an optical effect of the spectacle lens on a basis of the three-dimensional shape of the spectacle lens.

* * * * *